United States Patent [19]

Kamen

[11] Patent Number: 5,178,182
[45] Date of Patent: Jan. 12, 1993

[54] VALVE SYSTEM WITH REMOVABLE FLUID INTERFACE

[75] Inventor: Dean L. Kamen, Bedford, N.H.

[73] Assignee: DEKA Products Limited Partnership, Manchester, N.H.

[21] Appl. No.: 750,581

[22] Filed: Aug. 26, 1991

Related U.S. Application Data

[60] Division of Ser. No. 523,801, May 15, 1990, Pat. No. 5,088,515, which is a continuation-in-part of Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, which is a continuation-in-part of Ser. No. 836,023, Mar. 4, 1986, Pat. No. 4,778,451.

[51] Int. Cl.⁵ .................. F16K 27/02; F16K 31/02
[52] U.S. Cl. ................... 137/454.2; 251/129.06
[58] Field of Search .......... 137/15, 454.2, 315; 251/129.06

[56] References Cited

U.S. PATENT DOCUMENTS

| | | |
|---|---|---|
| 4,300,552 | 11/1981 | Cannon . |
| 4,340,083 | 7/1982 | Cummins .................. 251/129.06 X |
| 4,617,952 | 10/1986 | Fujiwara et al. .......... 251/129.06 X |
| 4,787,071 | 11/1988 | Kreuter et al. ............ 251/129.06 X |

Primary Examiner—Stephen M. Hepperle
Attorney, Agent, or Firm—Bromberg & Sunstein

[57] ABSTRACT

A valve having a disposable portion, which comes into contact with the fluid being controlled by the valve. The disposable portion has a valving chamber and a flexible membrane, which can seal off a mouth that is located on a protrusion in the chamber. The disposable portion is held by a fixture which uses a control gas or a mechanical actuator to apply pressure to the flexible membrane. The disposable portion may also have a pressure conduction chamber, which may be used to measure the flow rate of liquid through the disposable portion.

6 Claims, 5 Drawing Sheets

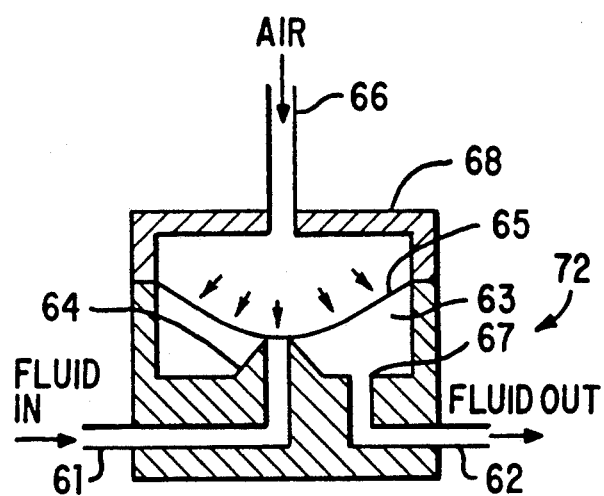
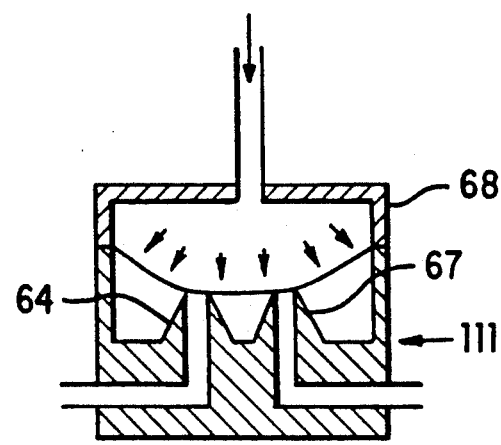
FIG. 1   FIG. 2
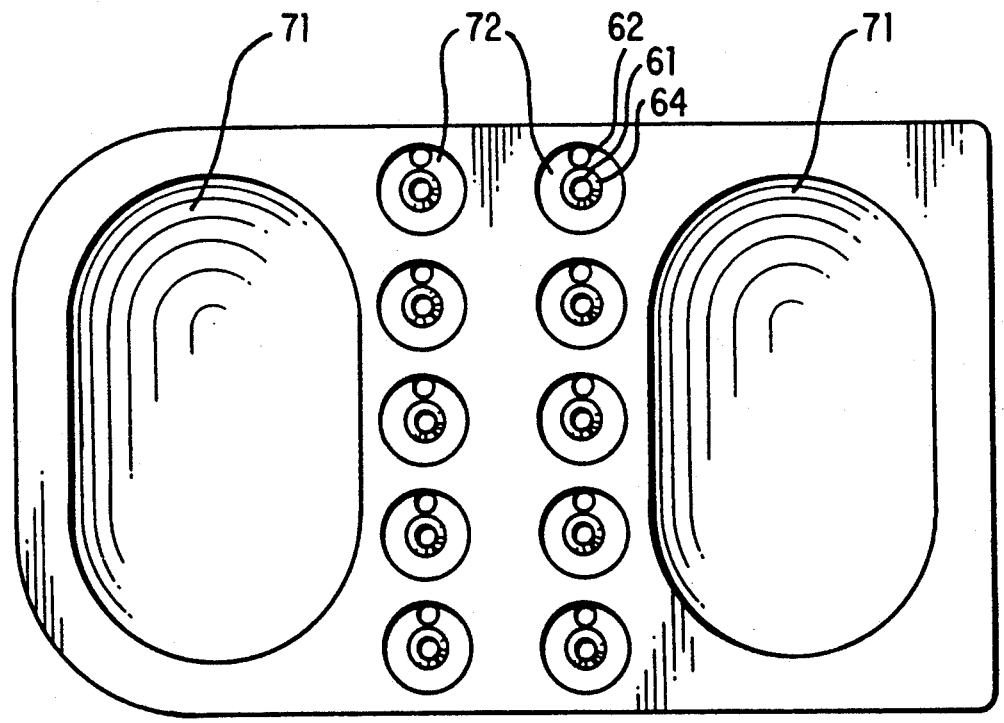
FIG. 3

VALVE SYSTEM WITH REMOVABLE FLUID INTERFACE

CROSS-REFERENCE TO RELATED APPLICATIONS

This is a divisional of application Ser. No. 523,801, filed May 15, 1990, issued as U.S. Pat. No. 5,088,515, which is a continuation-in-part of application Ser. No. 345,387, filed on May 1, 1989 (the "parent application") and issued as U.S. Pat. No. 4,976,162, which is a continuation-in-part of application Ser. No. 092,481, filed Sept. 3, 1987, issued as U.S. Pat. No. 4,826,482, which is a continuation-in-part of applications Ser. No. 022,167, filed Mar. 5, 1987, issued as U.S. Pat. No. 4,808,161 on Feb. 28, 1989, which is a continuation-in-part of Ser. No. 836,023, filed on Mar. 4, 1986, issued as U.S. Pat. No. 4,778,451 on Oct. 18, 1988. These related applications are hereby incorporated herein by reference.

BACKGROUND OF THE INVENTION

1. Field of the Invention

The present invention relates generally to systems for controlling fluid flow, and in particular to medical infusion technology, although other embodiments are possible.

2. Description of Related Art

Prior art systems for controlling the flow through an intravenous line typically act on the exterior of the standard intravenous tube. For instance, peristaltic pumps are used to pump intravenous fluid. These peristaltic pumps force the fluid through the line by squeezing the intravenous tube. Similarly, in order to restrict or cut off the flow of fluid, a clamp is used to squeeze the intravenous tube.

The advantage of these systems is that the pump or the clamp is not contaminated by coming into contact with the intravenous fluid. The intravenous fluid remains inside the intravenous line. Thus, the pump or the clamp does not need to be washed or sterilized between uses.

The disadvantage of these systems is that squeezing the standard intravenous tube is an inefficient way to control the flow through an intravenous line. It takes a great deal of force to squeeze and keep shut an intravenous tube. Additionally, after repeated or prolonged squeezings the intravenous tube tends to lose its rounded shape and become oblong in cross-section. Thus, even when it is desired to have unrestricted flow through the intravenous line, a tube that has undergone prolonged or repeated squeezings may restrict flow. Furthermore, a peristaltic pump that works on the outside of the intravenous tube cannot be used to deliver precise quantities of intravenous fluid.

SUMMARY OF THE INVENTION

The present invention provides a system for providing a valve for controlling flow of a fluid through a line (e.g., an intravenous line), wherein the portion of the valve that comes into contact with the fluid being controlled can be easily removed from the rest of the system and disposed of. This disposable portion is held against a fixture, which is that part of the system that is permanent and contains a control apparatus that opens and closes the valve. In certain embodiments the system may have more than one valve and may further have one or more pressure conduction chambers. As its name suggests, a pressure conduction chamber is used to transmit pressure to the fluid. As explained in the parent application, pressure may be applied to the fluid in order to measure the fluid flow rate. Alternatively, pressure may be applied to the fluid simply to force the fluid through the line, i.e., pumping the fluid (which may be done with positive or negative pressure). Preferably, the pressure conduction chamber is used for both flow measurement and pumping.

The disposable portion of the valve, i.e., the disposable conduit, contains a housing, through which a fluid path runs. The fluid path enters and exits the housing through at least two ports (one input and one output), which connect to the intravenous line. Disposed in the housing in the fluid path is at least one valving chamber. The fluid path enters and exits the valving chamber at two mouths. Preferably, at least one of the two mouths in the valving chamber is located on a protuberance from the surface of the housing. A flexible impermeable membrane is disposed on the surface of the housing and forms one of the sides of the valving chamber. The membrane is so disposed on the housing so that the flexible membrane can cover at least one of the mouths when a sufficient amount of pressure is applied to the side of the membrane facing away from the valving chamber. It is therefore preferred to locate at least one of the mouths opposite the flexible membrane, although the mouths could be oriented differently. The housing should be rigid enough so that the covering of the mouth by the flexible membrane can be reliably effected such that the membrane forms a seal over the mouth. If the housing is not rigid enough, it may be difficult to force the membrane to seal the mouth.

It may desired to use a disposable valve that would, in one mode, allow relatively unrestricted flow and, in another mode, merely restrict flow through the fluid conduit without completely stopping flow. To accomplish this, the geometry of the mouth may be altered so that, when the membrane is forced against the mouth, the mouth is not completely sealed, thereby allowing some flow through the conduit. A disposable conduit may contain two valves, one of which could be used to reduce flow, while the other could be used to stop flow through the fluid conduit.

In a preferred embodiment of the disposable conduit, the housing defines a pressure conduction chamber, located in the fluid path. Valving chambers may located between the pressure conduction chamber and each of the ports. A flexible impermeable membrane also defines one of the sides of the pressure conduction chamber. Preferably, different portions of the same sheet of flexible material can form the flexible membranes for all the valving chambers and pressure conduction chambers. In one embodiment, the housing is disposed in a bag made of flexible material, which forms the flexible membranes over the valving chambers and pressure conduction chambers.

The fixture, that part of the valving system that is permanent, includes a mechanism for holding the disposable fluid conduit in such a way that the disposable fluid conduit may be easily and quickly detached from the fixture (however, not so easily that the disposable fluid conduit may be detached accidently). The fixture also includes an apparatus for controlling the flow of fluid through the line. This control is accomplished by moving the membrane covering the valving chamber so that the membrane is alternately (i) forced against at least one of the mouths so as to prevent flow through the valving chamber and (ii) not so forced so that flow through the valving chamber is permitted. The fixture may apply a control fluid to the membrane; when the fixture increases the pressure of the control fluid, the membrane may be forced against at least one of the mouths, and when the fixture lowers the pressure of the control fluid, the membrane may be allowed to move away from the at least one mouth. Alternatively, an actuator may be used to apply pressure to the membrane. This actuator may include a piezoelectric bender. The fixture may also include an apparatus for transmitting pressure to the membranes covering the pressure conduction chambers. Preferably, this apparatus uses the same control fluid (e.g., air) that is used to control the valves in the disposable conduit for transmitting the pressure to the membrane covering the pressure conduction chamber. It will be appreciated that a microprocessor, or other electronic controller, is preferably used for regulating the pressure of the control fluid or the position of the actuator.

BRIEF DESCRIPTION OF THE DRAWINGS

FIGS. 1 and 2 show cross-sections of two different embodiments of the invention, including a fixture and a disposable portion with one valving chamber.

FIG. 3 shows a plan view of the rigid housing of a disposable cartridge having ten valving chambers and two pressure conduction chambers.

Like reference numerals refer to like items.

DESCRIPTION OF SPECIFIC EMBODIMENTS

Figure 5:
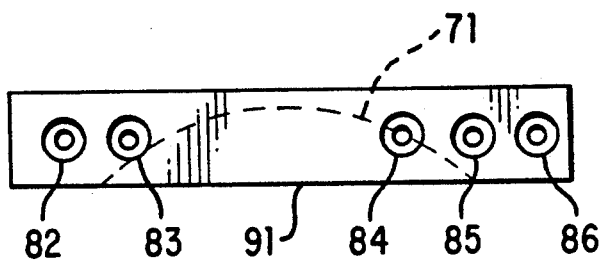
FIG. 5 shows an end view of the disposable cartridge of FIGS. 3 and 4.

A simple embodiment of the present invention is shown in FIG. 1, wherein a single valve is provided. The fluid path passes from the fluid line input 61 through the valving chamber 63 to the fluid line output 62. The valving chamber 63 is made of a rigid material, such as molded hard plastic. The fluid path enters the valving chamber 63 through a first mouth 64, which in this embodiment is located on a protuberance projecting from the wall of the valving chamber opposite the flexible membrane 65. The fluid path exits the valving chamber through a second mouth 69, which in this embodiment is flush with a wall of the valving chamber. FIG. 2 shows another embodiment, wherein both mouths, 64 and 67, are located on protuberances. Alternative (albeit nonpreferred) embodiments may have both mouths flush with a wall of the valving chamber or even on the sides of the valving chamber. In these embodiments the membrane needs to be more flexible, and it is more difficult to effect a seal over the mouth.

One wall of the valving chamber 63 is provided by a flexible impermeable membrane 65. This wall of the valving chamber is placed against a fixture 68, which provides a control fluid, preferably air, from a control fluid supply line 66 to the exterior surface of the membrane. The first mouth 64 is located with respect to the membrane 65 such that when the control fluid pressure is increased in the control fluid supply line 66 the flexible membrane 65 is urged against the mouth 64. Preferably, a material is chosen for the membrane 65 such that the membrane "grips" the mouth 64 in order to provide a better seal. (In an alternative embodiment, the geometry of the mouth would be altered so that the membrane would not completely seal it, thereby reducing, but not stopping, flow through the conduit. Such a valve may be built by cutting a notch in the protuberance that the mouth is located on.) In the FIG. 2 embodiment the second mouth 67 is also located opposite from the flexible membrane so that when the pressure of the control fluid is increased the flexible membrane is also urged against mouth 67. When it is desired to open the fluid path, the control fluid pressure is decreased until the fluid pressure in the fluid path pushes the membrane 65 away from the mouth 64, thereby permitting fluid to flow through the valving chamber. The protuberances may be made so that their height is adjustable, thereby allowing one to alter at what point the membrane would come into contact with the mouth.

The structure of these embodiments permits a mechanical advantage. The control fluid tends to distribute force all along the surface of the membrane 65. Because of the small diameter of the mouth 64, the fluid in the fluid input 61 acts on only a small area of the membrane 65, when the membrane is sealed against the mouth. Thus, the control fluid line pressure can produce more force on the membrane than the fluid input pressure (since force is equal to pressure times area). The FIG. 2 embodiment is useful if the output fluid may be highly pressurized, since the second mouth 67 in the this embodiment only permits a small area of the membrane to be exposed to the output fluid, when the membrane is sealed against the second mouth.

The pressure in the control fluid supply line may be controlled using a stepper motor employing a cam-actuated piston or other means known in the art. In a piston-based embodiment, a piston is used to compress the control fluid in the line, thereby increasing the control fluid pressure and causing the membrane to seal one or two of the mouths in the valving chamber. The piston is then retracted to decrease the control fluid pressure and thereby open the valve.

In an alternative embodiment the control fluid is stored in an airtight reservoir in communication with the control fluid line. A compressor is used to increase the control fluid pressure in the reservoir, and a solenoidoperated valve is used to open a communication pathway between the reservoir and the control fluid line, thereby increasing the pressure in the control line. (The foregoing is controlled by a microprocessor.) Alternatively, the reservoir may be pressurized using a hand pump. To open the valve in the disposable conduit, the communication pathway between the reservoir and the control fluid line is closed, and the control fluid line vented to ambient atmosphere.

The present invention provides numerous advantages. Primary among these advantages is the combination of mechanical reliability with low cost and ease of manufacture. The valving systems shown in FIGS. 1 and 2 are mechanically reliable because they have relatively few moving parts. The valving chamber 63 is fixed, as are the fluid line input 61, the fluid line output 62 and the control fluid line 66. The only moving parts are the control fluid pressure generating means and the flexible membrane 65. As discussed above, the control fluid pressure generating means may be implemented using a stepper motor and piston. Piston assemblies, because of the limited range of motion involved, are also mechanically reliable. As further discussed above, the control fluid pressure generating means may also be implemented using a pressurized air reservoir. The only moving parts in such an embodiment are the valve connecting the reservoir to the control fluid line, and the means used to pressurize the reservoir.

Further, the flexible membrane 65 may be made of any of a number of readily available, inexpensive materials, for example, the flexible plastic used to make intravenous bags. This material is known to be extremely rugged, in addition to being relatively inexpensive. Further, this plastic has excellent "gripping" properties.

Another advantage to using a membrane-based system is that there are none of the known disadvantages inherent in valving systems based on squeezing an intravenous tube. The first disadvantage in a squeezing system is that it is relatively difficult to obtain a perfect closing of the line. A relatively large amount of energy must be expended to pinch an intravenous line closed, because of the difficulty in "folding" the edges of a pinched tube. A further disadvantage is cold flow. An intravenous tube will, after repeated openings and closings, tend to change shape around the pinching site. This in turn decreases the mechanical reliability of the intravenous delivery system. None of these disadvantages are present in a membrane-based system. As discussed above, because of the mechanical advantage inherent in this system, relatively little energy is required to keep the valve closed. And because there is no pinching involved, cold flow does not present a significant problem.

Further, the device does not require precision molding. The valve will tolerate a broad range of manufacturing imperfections. For example, even if the valve chamber mouth is not perfectly aligned, the membrane will still seal against it. Even if the control fluid line is slightly off center, the membrane will still be urged against the valve chamber mouth. The only stringent requirements are that the valve chamber, including input and output lines, be fluid-tight, and that the control fluid line be airtight.

In addition, the utility of this valving system can be enhanced by the manufacturing method used. For example, the input line, valving chamber (including mouth), output line and membrane all may be constructed into a single disposable unit that may also include a pressure conduction chamber. The membrane may be attached to a rigid plastic structure that is sized to fit snugly onto a central flow control system unit. Alternatively, the valving system may be made integral with a drip chamber structure, which would be received by a specially adapted fixture.

In one embodiment of a flow control system, it is contemplated to mold the pressure conduction chamber together with input and output pathways and membrane-based valving chambers all out of the same block of plastic. The same sheet of membrane may be used as the membrane 65 in the valves and the pressure conduction chamber. Two such disposable units are depicted in FIGS. 3-5 and FIG. 7.

Figure 4:
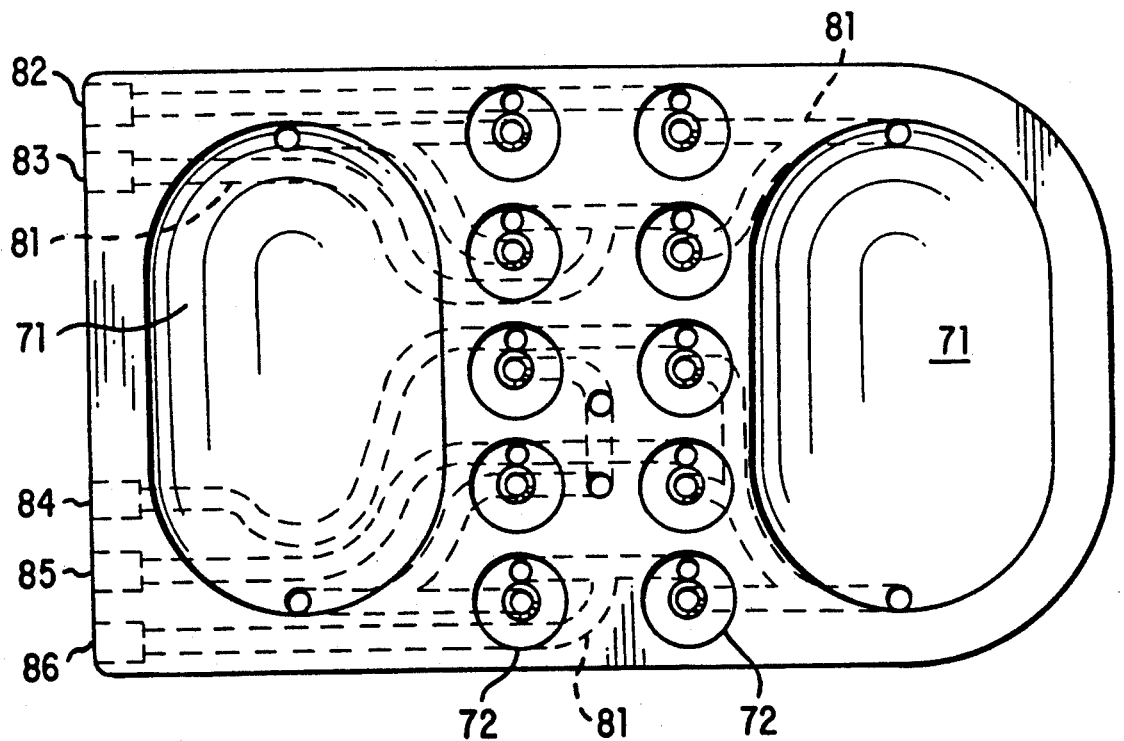
FIG. 4 shows a plan view of the disposable cartridge of FIG. 3 and its internal fluid paths.
Figure 6:
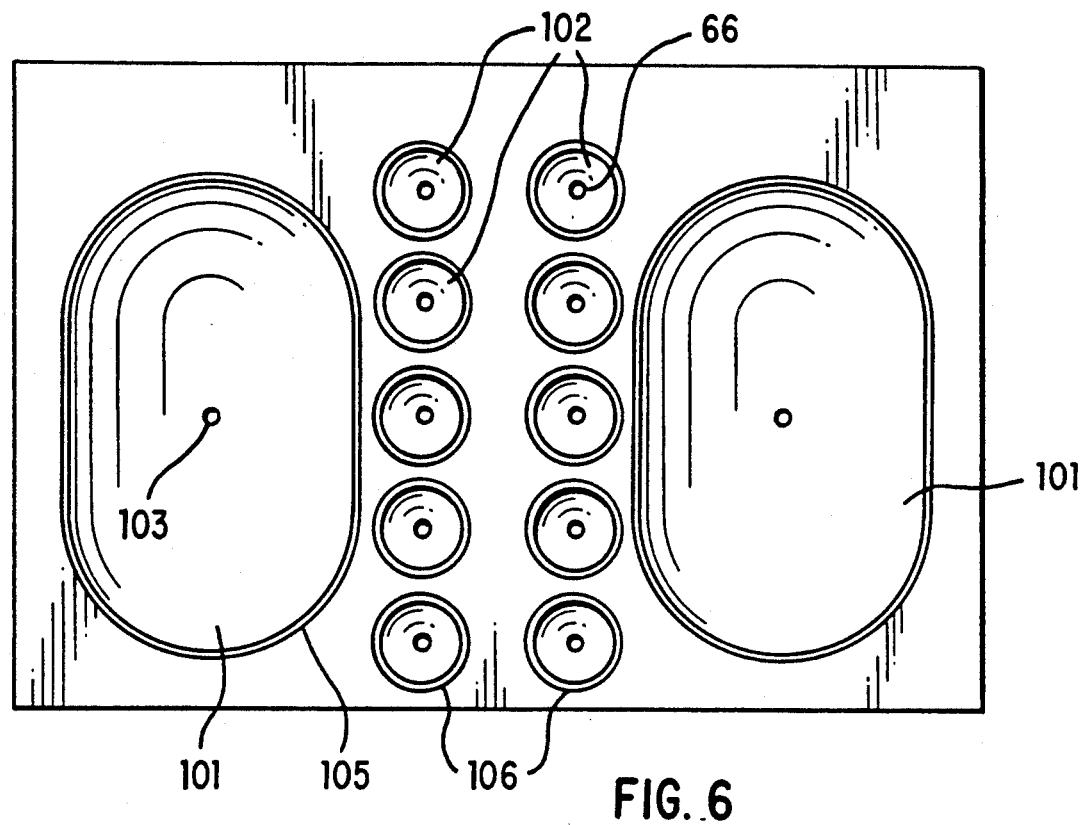
FIG. 6 shows a plan view of the face of the fixture, or central system unit, against which the disposable cartridge of FIGS. 3-5 is placed.

When being used to control flow, the disposable unit is affixed to a receiving block, such as that shown in FIG. 6, which is used with the disposable unit depicted in FIGS. 3-5. The housing unit may be held in place by a retaining clamp, or by other means known in the art. Sealing rings are provided to insure that the control fluid pathways, and the measurement gas pathways remain fluid-tight. In this embodiment, it is contemplated that the receiving block would be an integral part of the central flow control system unit. It will be seen that this is a desirable arrangement. The disposable unit is used to transport intravenous fluid, and must therefore be sterile. It would be impractical to clean and sterilize such a unit for multiple uses. The receiving block, on the other hand, must be sturdy, to insure a proper seal, and to insure proper operation of the valves.

The controller (i.e., the microprocessor) may be programmed to perform a safety protocol during calibration of the device to check that all the seals are tight. During such a protocol, control fluid pressure to various valving chambers may be manipulated, and the resulting pressure changes may be monitored using the pressure transducers in the central flow control system unit. Aberrant conditions would cause an alarm state to be entered into.

Not all pathways would be required for all applications of the controller unit. A "universal" housing unit that would embody all possible pathway configurations for various situations may be designed and manufactured. The receiving block would be adapted for specific controller applications. Alternatively, the microprocessor could be programmed to valve off pathways, as required.

FIG. 3 shows one embodiment of a disposable housing unit (or "cartridge" or "cassette"). This particular unit has two concave indentations 71 for pressure conduction chambers, so that two fluid control systems may function in parallel. In a preferred embodiment, two fluid control systems are used to deliver intravenous fluid to a patient in order to make the flow of fluid smoother. As one container 71 is dispensing, the other is filling. Thus, fluid is delivered in more closely spaced and smaller pulses, rather than larger pulses that come less frequently and that have longer periods between them.

The disposable cartridge shown in FIG. 3 also has ten valves 72 of the type depicted in FIG. 1, with the input 61 and the output 62 showing. This side of the unit has a membrane stretched across and attached to it that serves as the membrane (65 in FIG. 1) for the valves 72 and the membrane for the pressure conduction chamber 71. (See item 91 in FIG. 5.)

FIG. 4 shows a bottom view of the disposable cartridge showing the internal piping or passageways 81, which are inside the disposable cartridge and which connect the various valves 72, the container indentations 71 and the various inputs and outputs 82-86. The inputs and outputs may be arranged in a variety of ways; for example, the top two ports 82 and 83 may both be inputs coming from two different fluid supplies, the bottom two ports 85 and 86 may be outputs. Port 84 could be used to remove samples of the fluid from the container for testing or analyzing or to add additional medication to the intravenous fluid. FIG. 5 shows an end view of these ports 82-86, as well as the fluid side of the containers 71 in phantom. The membrane 91 for the valves 72 and the containers 71 is attached to the disposable cartridge on the side indicated. The membrane 91 billows in and out depending on how much fluid is in the container.

FIG. 6 shows the face of the flow control system unit, against which the disposable shown in FIGS. 3-5 is placed and held by a clamping device. There are two large indentations 101 on the system unit to match the indentations 71 on the disposable. These indentations 101 on the system unit can contain a measurement gas for measuring the fluid flow rate. Each indentation has an aperture 103, through which measurement gas passes. The measurement gas can be used to measure how much of the complete container is not occupied by the fluid (when the container is isolated) and thereby permit measurement of the fluid flow rate, as well as to suction fluid into the container, and to force fluid out of the container.

FIG. 6 also shows receptacles, or dimples, 102 for the valves 72 and an aperture 66, through which the valve control fluid passes. The pressure conduction chamber indentations 101 and the valve receptacles 102 are surrounded by seals, 105 and 106 respectively, so that when the disposable is clamped against the system unit an air-tight seal is formed.

Figure 7:
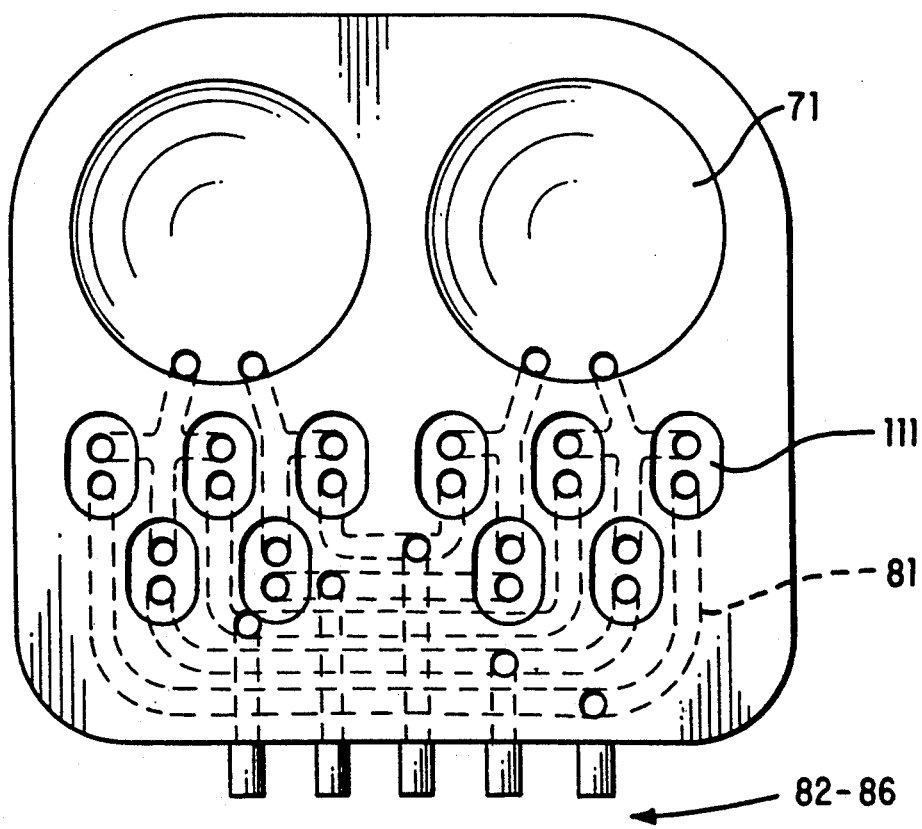
FIG. 7 shows a plan view of an alternative disposable cartridge and its internal fluid paths.

FIG. 7 shows an alternative disposable housing unit that like the disposable housing unit in FIGS. 3-5 has container indentations 71, fluid pathways 81 and input-/output ports 82-86. The FIG. 7 disposable, however, uses the valves 111 shown in FIG. 2. Despite this difference and the different piping layout, the FIG. 7 disposable functions the same way as the disposable in FIGS. 3-4.

Figure 8:
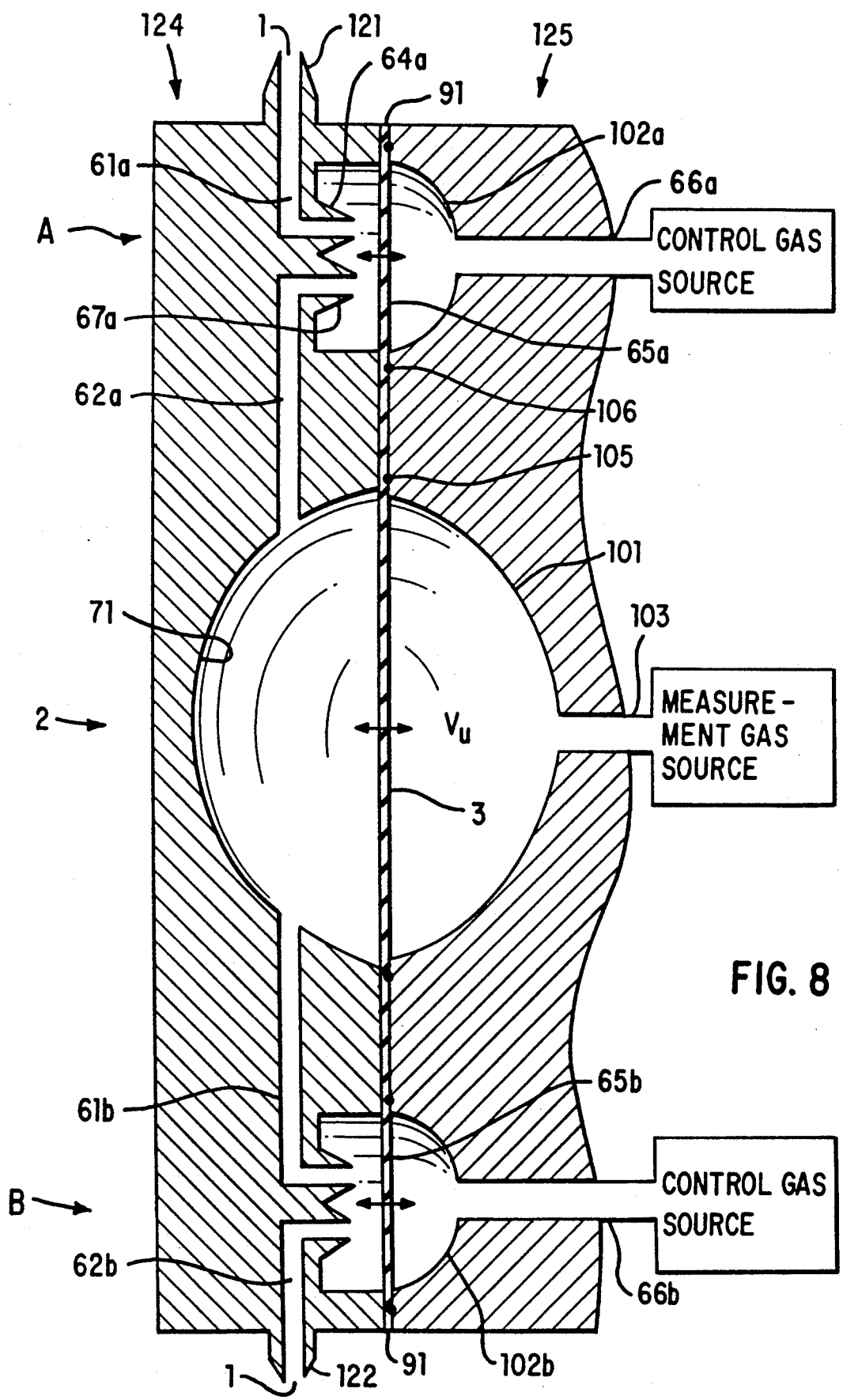
FIG. 8 shows a cross-section of another alternative disposable in contact with a fixture.

FIG. 8 shows a simple embodiment of the disposable housing unit 124 clamped against the face of the central flow control unit 125 designed for this disposable 124. This disposable 124 has only one pressure conduction chamber 2 and two valves, A and B. The input 61a of valve A is connected to the intravenous line 1 by a protrusion 121, which can be inserted in the intravenous tubing. Valve A and valve B are of the type depicted in FIG. 2; the two beveled mouths 64a and 67a can be seen in valve A. The output 62a of valve A leads in to the left half of the pressure conduction chamber 2, which is formed by the indentation 71 in the disposable 124. Membrane sheet 91 is attached to the disposable 124 and covers the whole side of the disposable. Parts of this membrane sheet 91 function as the membrane 65a for valve A, the membrane 3 in the pressure conduction chamber 2, and the membrane 65b in valve B. Valve A is disposed against a receptacle 102a in the central unit 125, which is connected to an air supply 66a through which air is pumped back and forth, thereby effecting the opening and closing of valve A by pulling the membrane 65a back from the mouths 64a and 67a and pushing the membrane 65a against mouths 64a and 67a. In this case, the air is functioning as the valve control fluid.

Channel 103 provides a path for the measurement gas (which can be air) from the pressure conduction chamber 2 to the rest of the system (including, for example, the reservoir). The membrane 3, which, as noted above, is part of the flexible sheet 91, moves back and forth depending on how much fluid is in the pressure conduction chamber 2. Because the pressure is changed frequently during flow measurement cycles, the temperature of the measurement gas may fluctuate. Such temperature fluctuations may affect the accuracy of flow measurement. In order to stabilize the temperature, it may be desired to place steel or copper wool in the channel 103 to act as a heat sink.

The pressure conduction chamber 2 is connected to the input 61b of valve B, which is disposed against the receptacle 102b and which functions the same way as valve A by means of air supply 66b. The output 62b flows into the intravenous line 1 connected to the patient. A protrusion 122 is used to attach the tube to the disposable 124.

In order to ensure the proper sealing between the elements of the disposable, gasket-like seals, 105 and 106, are disposed around the container and the valves.

Figure 9:
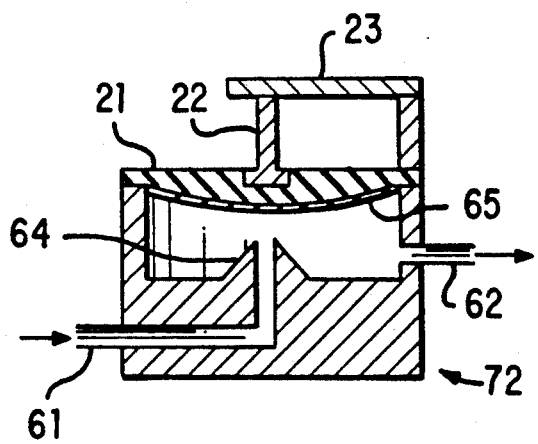
FIG. 9 shows a cross-section of an embodiment of the invention, including a fixture using piezo-electric benders and a disposable portion with one valving chamber, wherein the valve is open.
Figure 10:
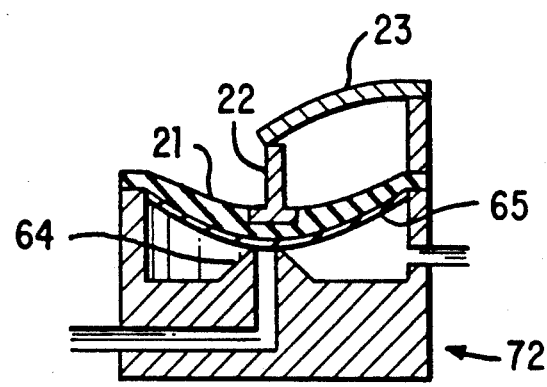
FIG. 10 shows a cross-section of the embodiment shown in FIG. 9, wherein the valve is closed.

FIGS. 9 and 10 show an alternative embodiment of the system, wherein FIG. 9 shows the valve open and FIG. 10 shows the valve closed. The disposable portion 72 of the valve is very similar to the disposable portion of the valve shown in FIG. 1. The fixture, however, is different. Instead of using a control fluid to move the membrane 65, the fixture uses an actuator to apply a force to the membrane. The face of the fixture is made of a flexible, yet durable, material 21. An actuator moves the face of the fixture, so that it alternately forces the membrane 65 against the mouth 64 in the valving chamber and allows the membrane 65 to move away from the mouth 64. The embodiment shown in FIGS. 9 and 10 use a bender 23 made of piezoelectric material. In FIG. 9 the bender 23 is in its normal position. In FIG. 10 the bender 23 is actuated by an electric potential, thereby bending the bender 23 and forcing the rod 22 down so that the face of the fixture forces the membrane 65 over the mouth 64. Conversely, the bender may be set so that in its normal position it forces the membrane over the mouth, and when actuated by an electric potential the bender pulls back the face of the fixture, thereby allowing the membrane to move off of the mouth.

Figure 11:
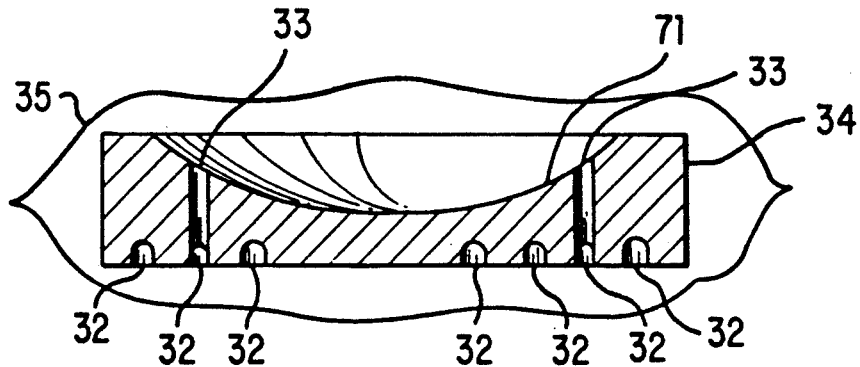
FIG. 11 shows a cross-section of a preferred embodiment of the disposable conduit, wherein the rigid housing is placed in a bag.

FIG. 11 shows a cross-section of a preferred embodiment of the disposable conduit. In this embodiment a relatively rigid housing 34 is placed inside a bag 35 made of a flexible, impermeable material. The bag needs at least one opening through which the ports of the housing may pass and be connected to the intravenous line. Preferably, the opening of the bag is formed relatively tightly around the ports of the housing, so that fluid spillage is minimized when the intravenous line is disconnected from the disposable conduit. A pressure conduction chamber 71, as well as any valving chambers (not shown) or any other pressure conduction chambers (not shown), are located on the top side of the housing 34. Fluid paths 32 are formed as grooves on the underside of the housing. Additional groovelike fluid paths may be placed in the top side of the fluid housing. Some groove-like fluid paths 32 may be connected to the pressure conduction chamber 71 by means of vertical paths 33.

Figure 12:
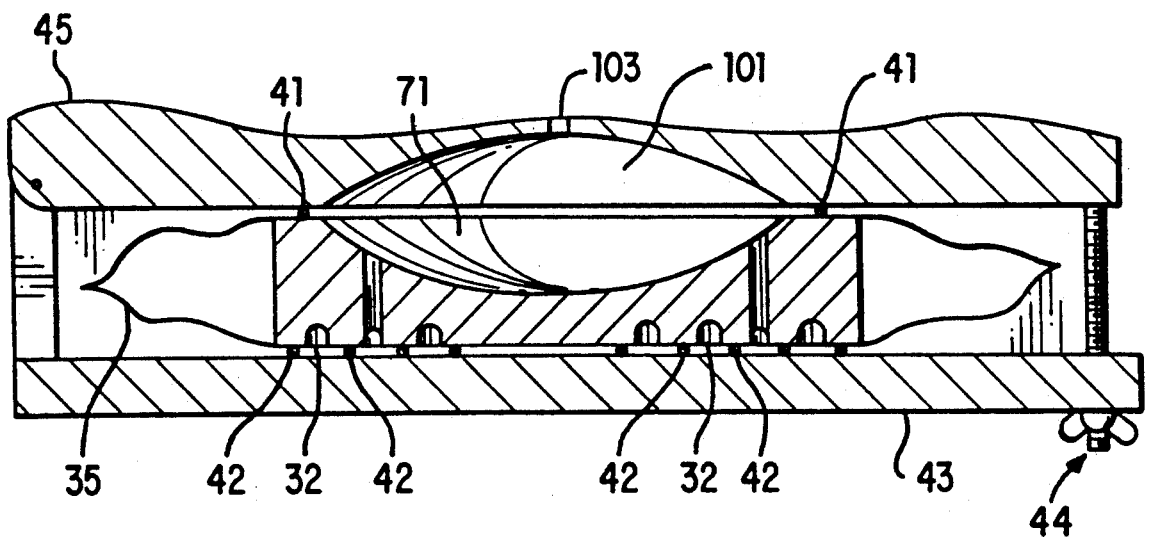
FIG. 12 shows a cross-section of the disposable conduit shown in FIG. 11 and a fixture for holding the disposable conduit.

In FIG. 12 the disposable fluid conduit of FIG. 11 is held against a fixture 45 by means of a clasp 43, which at one end is hingedly attached to the fixture 45 and at the other end may held to the fixture 45 by means of a threaded screw and nut 44 or some other type of quick-release fastening means that is able to apply sufficient force to the disposable fluid conduit while holding the conduit. A gasket 41 on the fixture serves to seal the bag 35 around the pressure conduction chamber 71. Thus, a portion of the bag forms the membrane on the pressure conduction chamber. Another gasket 42 is placed on the clasp portion 43 of the fixture, so as to form seals around the groove-like fluid paths 32. If any groove-like fluid paths are located on the top side of the housing, the gasket on the face of the fixture may be shaped so as to form seals around these groove-like fluid paths. The clasping portion of the fixture 43 must be able to exert enough force on the disposable fluid conduit, so that the gasket may create effective seals. This type structure is preferred, because it is much easier to manufacture a housing 34 with groove-like fluid paths 32 on its surface than to manufacture a housing with fluid paths encased inside the housing. Thus, the bag 35, in addition to forming the membrane on the pressure conduction chambers and the valving chambers, is also used to seal the groove-like fluid paths so that fluid does not leak from one fluid path 32 into an adjacent fluid path 32.

What is claimed is:

1. A system for providing a valve in a line that delivers liquid, such that the portion of the valve that comes into contact with the liquid in the line may be easily disposable, the system comprising:
   a housing;
   a first flexible membrane disposed on the housing, the first flexible membrane having an internal side facing the housing and an external side facing away from the housing, the housing and the first flexible membrane defining a valving chamber;
   a liquid path passing through the housing from a first port through the valving chamber to a second port so as to provide liquid communication between the valving chamber and the line, the path entering the valving chamber at first and second mouths, wherein at least one of said mouths inside the valving chamber protrudes from one side of the housing towards the membrane;
   a fixture for holding the housing, such that the housing may be easily disengaged from the fixture;
   first pressure means, disposed in the fixture, for alternately (i) providing pressure to the external side of the first flexible membrane so as to force the first flexible membrane against the protruding mouth and (ii) relieving pressure on the external side of the first flexible membrane so as to permit relatively unrestricted flow through the liquid path through the valving chamber, wherein the first pressure means includes a mechanical actuator located in the fixture adjacent to the first flexible membrane;
   a second flexible membrane disposed on the housing, the second flexible membrane having an internal side facing the housing and an external side facing away from the housing, the housing and the second flexible membrane defining a pressure conduction chamber disposed in the liquid path, and
   second pressure means, disposed in the fixture, for alternately (i) providing pressure to the external side of the second flexible membrane in the region of the pressure conduction chamber and (ii) relieving pressure on the external side of the second flexible membrane in the region of the pressure conduction chamber.

2. A system according to claim 1, wherein the housing is disposed in a bag, the bag having at least one opening to permit fluid communication between the line and the fluid path and forming the first and second flexible membranes.

3. A system according to claim 1, further including a third flexible membrane disposed on the housing, wherein the third flexible membrane and the housing define a second valving chamber disposed in the fluid path such that the fluid path first passes through one valving chamber, then the pressure conduction chamber and then the other valving chamber.

4. A fluid conduit according to claim 1, wherein a single sheet of flexible material forms the first and second flexible membranes.

5. A system for providing a valve in a line that delivers liquid, such that the portion of the valve that comes into contact with the liquid in the line may be easily disposable, the system comprising:
   a housing;
   a first flexible membrane disposed on the housing, the first flexible membrane having an internal side facing the housing and an external side facing away from the housing, the housing and the first flexible membrane defining a valving chamber;
   a liquid path passing through the housing from a first port through the valving chamber to a second port so as to provide liquid communication between the valving chamber and the line, the path entering the valving chamber at first and second mouths, wherein at least one of said mouths inside the valving chamber protrudes from one side of the housing towards the membrane;
   a fixture for holding the housing, such that the housing may be easily disengaged from the fixture; and
   first pressure means, disposed in the fixture, for alternately (i) providing pressure to the external side of the first flexible membrane so as to force the first flexible membrane against the protruding mouth and (ii) relieving pressure on the external side of the first flexible membrane so as to permit relatively unrestricted flow through the liquid path through the valving chamber;
   wherein the first pressure means includes a mechanical actuator located in the fixture adjacent to the first flexible membrane, and
   wherein the housing is disposed in a bag, the bag having at least one opening to permit fluid communication between the line and the fluid path and forming the first flexible membrane.

6. A system for receiving a disposable liquid conduit, the liquid conduit having a housing, a first flexible membrane disposed on the housing and a valving chamber defined by the first flexible membrane and the housing, and a pressure conduction chamber defined by the housing and a second flexible membrane disposed on the housing, the system forming with the liquid conduit a valve in a line that delivers liquid, the system comprising:
   a fixture for holding the liquid conduit, such that the disposable liquid conduit may be easily disengaged from the fixture;
   first pressure means, disposed in the fixture, for alternately (i) providing pressure to the first flexible membrane so as to restrict flow through the liquid path through the valving chamber and (ii) relieving pressure on the flexible membrane so as to permit relatively unrestricted flow through the liquid path through the valving chamber, wherein the first pressure means includes a mechanical actuator disposed adjacent to the first flexible membrane, such that the actuator, in a first position, applies a force to the flexible membrane and, in a second position, is located closer to the fixture; and second pressure means, disposed in the fixture for providing pressure to the second flexible membrane, wherein the second pressure means includes means, located in the fixture, for (a) providing a gas to an area adjacent to the second flexible membranes and (b) changing the pressure of the gas, wherein the actuator includes a piezoelectric bender.

* * * * *